United States Patent
Cramp

[11] Patent Number: 6,013,839
[45] Date of Patent: Jan. 11, 2000

[54] PROCESS FOR PREPARING 2-(THIOSUBSTITUTED)-4-HALOACETOPHENONES

[75] Inventor: Susan Mary Cramp, Ongar, United Kingdom

[73] Assignee: Rhone-Poulenc Agriculture Limited, Ongar, United Kingdom

[21] Appl. No.: 09/125,313
[22] PCT Filed: Feb. 10, 1997
[86] PCT No.: PCT/EP97/00606
§ 371 Date: Nov. 4, 1998
§ 102(e) Date: Nov. 4, 1998
[87] PCT Pub. No.: WO97/30026
PCT Pub. Date: Aug. 21, 1997

[30] Foreign Application Priority Data

Feb. 15, 1996 [GB] United Kingdom ............ 9603127

[51] Int. Cl.[7] .................................. C07C 319/14
[52] U.S. Cl. .................. 568/43; 568/22; 568/24; 568/25; 568/42
[58] Field of Search ............... 568/22, 24, 25, 568/43, 42

[56] References Cited

FOREIGN PATENT DOCUMENTS

| | | |
|---|---|---|
| 0418175 | 3/1991 | European Pat. Off. |
| 0487357 | 5/1992 | European Pat. Off. |
| 0527036 | 2/1993 | European Pat. Off. |
| 0536512 | 4/1993 | European Pat. Off. |
| 0560482 | 9/1993 | European Pat. Off. |
| 0609798 | 8/1994 | European Pat. Off. |
| 1415295 | 11/1975 | United Kingdom . |
| 1475890 | 6/1977 | United Kingdom . |
| 94/18179 | 8/1994 | WIPO . |

OTHER PUBLICATIONS

CA:109:170526 by Anderson, J Org Chem, 53(13), pp. 3125–3127, 1988.
CA:114:122954 by Marriott, Tetrahedron Lett. 31(51), 7485–8, 1990.
CA:125:10525 by Hoepping, Phosphorus, Sulfur Silicon Rela Elements 107(1–4) pp. 285–288, 1995.
WPI/Derwent Abstract No. 96–318910—abstract of JP 08 143534 (1996).
Cooper et al, *Synthetic Communications*, 25(6), pp. 899–906 (1995).
Fink et al, *Tetrahedron Letters*, 34(41), pp. 6525–6528 (1993).
March, *Advanced Organic Chemistry*, fourth edition, pp. 250–251 (1992).
March, *Advanced Organic Chemistry*, 3rd edition, John Wiley & Sons, New York, New York, pp. 576–578 (1985).
Hoepping et al, *Phosphorous, Sulfur, and Silicon*, vol. 107, pp. 285–288 (1995).

*Primary Examiner*—Gary Geist
*Assistant Examiner*—Jean F Vollano
*Attorney, Agent, or Firm*—Burns, Doane, Swecker & Mathis, L.L.P.

[57] ABSTRACT

The invention relates to a process for preparing a 2-(thiosubstituted)-4-haloacetophenone such as those of formula (I), which comprises reacting a 2,4-dihaloacetophenone with a thiolating agent under substantially anhydrous conditions. In formula (I), $R^1$ and $R^2$ have the meanings given in the description and $R^3$ is halogen. The compounds prepared are useful as intermediates in the preparation of herbicidally active compounds.

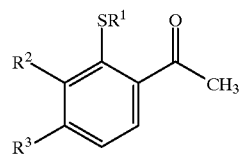

(I)

27 Claims, No Drawings

PROCESS FOR PREPARING 2-(THIOSUBSTITUTED)-4-HALOACETOPHENONES

This application is the national phase of PCT/EP97/00606, filed Feb. 10, 1997, now WO97/30026.

This invention relates to a process for preparing certain 2-thiosubstituted acetophenone derivatives, which are useful as intermediates in the preparation of herbicidally active compounds.

Cooper et al, Synthetic Communications, Vol. 25(6), pages 899–906 (1995) describe the preparation of 2-ethylthio-4-chlorobenzamides and 2-ethylthio-3,4-dichlorobenzamides by reacting the corresponding 2,4-dichloro- and 2,3,4-trichlorobenzamides respectively with ethanethiol in N,N-dimethyl formamide (DMF) in the presence of potassium carbonate. These reactions were reported as proceeding with ortho-selectivity, except where the benzamide was a tertiary amide. Fink et al, Tetrahedron Letters. Vol. 34(41) pages 6525–6528 (1993) describe the preparation of 4-fluoro-2-(phenylmethylthio)acetophenone from 2,4-difluoroacetophenone. The reaction is performed in tetrahydrofuran (THF) with benzyl mercaptan and potassium t-butoxide. This is described as proceeding in a yield of 63% with a ratio of ortho/para products of 8.6:1 (i.e. 89% ortho, 11% para). It is however desirable to provide intermediates which are used in multi-step reaction schemes in high yields and with high isomeric purity.

It is therefore an object of this invention to provide a process for preparing 2-thiosubstituted acetophenones proceeding in high yield.

It is a further object of this invention to provide an improved process for preparing 2-thiosubstituted acetophenones with a greater ortho selectivity.

Surprisingly, the present invention allows these objects to be met in whole or in part.

Thus, the present invention provides a process for preparing a 2-(thiosubstituted)-4-(halo)acetophenone which comprises reacting a 2,4-(dihalo)acetophenone with a thiolating agent under substantially anhydrous conditions, optionally in the presence of a base.

Surprisingly, it has been found that the reaction proceeds in good yield and with high regioselectivity under such conditions.

It will be understood that the halogen atoms in the 2,4-(dihalo)acetophenone may be the same or different, and that the acetophenone may be optionally substituted by from one to three groups in the 3- and/or 5- and/or 6-positions of the benzene ring.

By the term "substantially anhydrous" is meant that water not deliberately introduced into the reaction mixture (e.g. the thiolating agent used is not provided in an aqueous solution or suspension). Generally the reaction takes place with less than about 5% by volume water content, preferably less than about 2%, even more preferably less than about 1%, typically from about 0.01 to about 0.5%. It will however be understood that in certain cases slightly more or less water may be tolerated, depending on the nature of the solvents used, the 2-thiosubstituted acetophenone derivative to be prepared and other reaction conditions.

The reaction is preferably performed in an ether solvent such as THF, diisopropyl ether, tert-butyl methyl ether (MTBE), diglyme and diethyl ether. Preferred solvents are THF, diisopropyl ether and MTBE, the latter two being preferred when the process is performed on a large scale, for reasons of cost and availability.

Preferably the 2-(thiosubstituted)-4-haloacetophenone is a compound of formula (I):

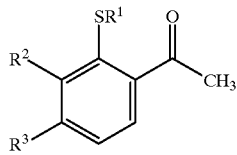

(I)

wherein
$R^1$ is lower alkyl, or phenyl optionally substituted by from one to five groups which may be the same or different selected from halogen, lower alkyl, lower haloalkyl, lower alkoxy, lower haloalkoxy and $—S(O)_nR^5$;
$R^2$ is hydrogen, halogen, lower alkyl, lower haloalkyl, lower alkoxy, lower haloalkoxy or $—S(O)_nR^5$;
$R^3$ is halogen; n is zero, one or two; and
$R^5$ is lower alkyl or phenyl optionally substituted by from one to five groups which may be the same or different selected from halogen, lower alkyl, lower haloalkyl, lower alkoxy, lower haloalkyl and $—S(O)_n$-alkyl;
the 2,4-dihaloacetophenone is a compound of formula (II):

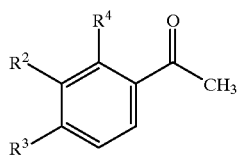

(II)

where $R^2$ and $R^3$ are as defined above and $R^4$ is halogen;
and the thiolating agent is a compound of formula (III):

$$R^1S—X \qquad (III)$$

wherein $R^1$ is as defined above and X is hydrogen or a metal cation.

By the term 'lower' is meant radicals comprising at least one hydrocarbon chain, it being understood that such radicals contain from one to six carbon atoms linked together in a straight- or branched-carbon chain.

In a preferred aspect of the invention each of $R^2$, $R^3$ and $R^4$ are chlorine.

In another preferred aspect of the invention $R^3$ and $R^4$ are halogen (preferably chlorine) and $R^2$ is hydrogen.

In another preferred embodiment $R^2$ is selected from hydrogen, halogen, lower alkoxy (e.g. methoxy) and lower haloalkoxy (e.g. 2,2-difluoroethoxy).

Preferably $R^1$ is lower alkyl (most preferably methyl).

X is preferably hydrogen or an alkaline earth metal or alkali metal cation (e.g. lithium or sodium). Where X is hydrogen the presence of a base is preferred, for example an alkali or alkaline earth base (such as sodium hydride, potassium carbonate or potassium t-butoxide).

The reaction is generally performed at a temperature from −80° C. to the boiling of the solvent, more preferably from −20 C. to 60° C., from about 10° to about 55° being especially preferred.

The molar ratio of the 2,4dihaloacetophenone:thiolating agent is generally from 1:1 to 1:2, preferably from 1:1 to 1:1.5, even more preferably from 1:1.1 to 1:1.3.

The following non-limiting examples illustrates the invention.

EXAMPLE 1

Preparation of 3,4-dichloro-2-(methylthio)acetophenone (small scale)

Sodium thiomethoxide (0.2 g, 0.0028M) was added to a solution of 2,3,4-trichloroacetophenone (0.5 g, 0.0022M) in THF (10 ml). The mixture was stirred at room temperature for 3 hours then diluted with diethyl ether, washed with water, dried over magnesium sulphate, filtered and evaporated to give 3,4-dichloro-2-(methylthio)acetophenone (0.43 g, 82%) as a yellow oil, $H^1$ NMR ($CDCl_3$) 2.4(s,3H), 2.6(s,3H), 7.15(d,1H), 7.5(d,1H). NMR analysis indicated that there was less than 1% of the para product present.

By proceeding in a similar manner were prepared:

4chloro-2-(methylthio)acetophenone as a fawn solid, m.p.63° C., NMR analysis indicated a purity >98%, starting from 2,4-dichloroacetophenone; and 4-bromo-3-(2,-difluoroethoxy)-2-(methylthio) acetophenone as a red oil,, $H^1$ NMR ($CDCl_3$) 2.45(s, 3H), 2.6(s,3H), 4.3(t,d,2H), 6.25(t,t, 1H), 7.05(d,1H), 7.55(d,1H), starting, from 2,4-dibromo-3-(2,2-difluoroethoxy)acetophenone. NMR analysis indicated a purity >98%.

EXAMPLE 2

Preparation of 3.4-dichloro-2-(methylthio)acetophenone (larger scale)

2,3,4-Trichloroacetophenone (20.03 g, 89.6 mM) was dissolved in THF (200 ml) and dry sodium thiomethoxide (8.06 g, 115.1 mM) was added. The mixture was stirred for 6.8 hours at 25° C. Water (100 ml) and MTBE (100 ml) were then added and the resulting two phases separated. The aqueous phase was re-extracted with MTBE (100 ml) and the combined organic phases were washed with brine (2×50 ml). The solvent was removed under reduced pressure to give of 3,4-dichloro-2-(methylthio)acetophenone as a brown liquid (20.70 g, 94% yield). Less than 1% of the para isomer was detected.

EXAMPLE 3

The effect of the presence was analysed in the following experiment. The conditions of Example 1 were repeated replacing 2,3,4-trichloroacetophenone with 2,4-dichloroacetophenone [to give 4-chloro-2-(methylthio) acetophenone], except that the reaction mixture was stirred overnight and the THF (which had less than 0.1% by volume water content when received from the suppliers and which was stored over 4 Angstrom molecular sieves) was evaporated prior to work up. Various quantities of water were added and the reaction yield and regioselectivity determined (the approximate proportion of each regioisomer present was determined by measuring $H^1$ NMR peaks).

The following results were obtained. Note that in Tables 1 and 2 below 'SM' means starting material (i.e. 2,4-dichloroacetophenone), 'Prod' means desired product (i.e. 4-chloro-2-(methylthio)acetophenone) and 'Isomer' means the para-product (i.e. 2-chloro-4-(methylthio) acetophenone). The percentages for the water are by volume and the percentages for the compounds are based on the theoretical yield from the starting material.

TABLE 1

| | Percentage present | | | Ratio |
|---|---|---|---|---|
| % Water | SM | Prod | Isomer | Prod:Isomer |
| <0.1 | Trace | >99% | Trace | >99:1 |
| 0.5 | <1% | >98% | <1% | >98:1 |
| 1.0 | 15 | 84 | 1 | 84:1 |

TABLE 1-continued

| | Percentage present | | | Ratio |
|---|---|---|---|---|
| % Water | SM | Prod | Isomer | Prod:Isomer |
| 2.0 | 51 | 48.5 | 0.5 | 97:1 |
| 5.0 | 95 | 5 | Trace | >5:1 |
| 10.0 | 98 | 2 | Trace | >2:1 |

This indicates that at higher concentrations of water, the reaction did not proceed to completion at room temperature.

EXAMPLE 4

The effect of the heating the reaction and the presence of water was analysed in the following experiment. The conditions of Example 3 were repeated, except that the reaction mixture was heated at from about 50° C. to about 55° C. overnight.

The following results were obtained:

TABLE

| | | % obtained | | Ratio |
|---|---|---|---|---|
| % Water | SM | Prod | Isomer | Prod:Isomer |
| <0.1 | Trace | >99% | Trace | >99:1 |
| 0.5 | Trace | >99% | Trace | >99:1 |
| 1.0 | 7% | 93% | Trace | >93:1 |
| 2.0 | 38% | 60% | 2.50% | 25:1 |
| 5.0 | 52% | 40% | 8% | 5:1 |
| 10.0 | 71% | 22% | 7% | 3.2:1 |
| 20.0 | 78% | 13% | 9% | 1.5:1 |
| 50.0 | 80% | 10% | 10% | 1:1 |

These results show that at higher reaction temperatures, the regioselectivity decreases significantly when the reaction is performed in the presence of substantial quantities of water.

The above experiments therefore clearly demonstrate the advantage of the process of the invention over the prior art, both in terms of a higher yield and a greater selectivity, and the effect of water on the reaction.

The compounds obtained by the process of the present invention may be used in the preparation of herbicidally active compounds for example, as part of one of the following reaction schemes:

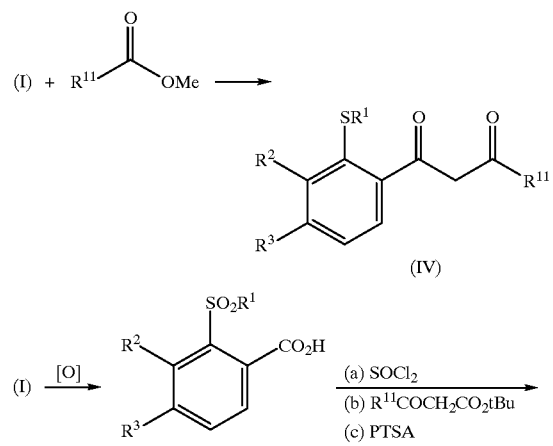

-continued

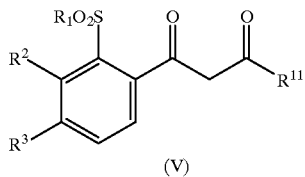

Compounds of formulae (IV) and (V) are known the literature as intermediates in the preparation of herbicidally active compounds. Both the diones of formula (V) above and the herbicidally active compounds which they be used to prepare are described, for example, in European Patent Publication Nos. 0418175, 0487357, 0527036, 0560482, 0609798 and 0682659.

What is claimed:

1. A process for preparing a 2-(thiosubstituted)-4-haloacetophenone of formula (I):

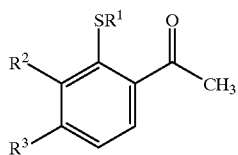

wherein
- $R^1$ is lower alkyl, or phenyl which is unsubstituted or substituted by from one to five groups which are the same or different selected from the group consisting of halogen, lower alkyl, lower haloalkyl, lower alkoxy, lower haloalkoxy and $-S(O)_n R^5$;
- $R^2$ is hydrogen, halogen, lower alkyl, lower haloalkyl, lower alkoxy, lower haloalkoxy or $-S(O)_n R^5$;
- $R^3$ is halogen; n is zero, one or two;
- $R^5$ is lower alkyl or phenyl which is unsubstituted or substituted by from one to five groups which are the same or different selected from the group consisting of halogen, lower alkyl, lower haloalkyl, lower alkoxy, lower haloalkoxy and $-S(O)_n$-alkyl;

said process comprising reacting a 2,4-dihaloacetophenone of formula (II):

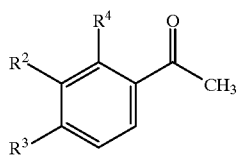

wherein $R^2$ and $R^3$ are as defined above and $R^4$ is halogen; with a thiolating agent of formula (III):

 $R^1S-X$ (III)

wherein $R^1$ is as defined above and X is hydrogen or a metal cation;
under substantially anhydrous conditions in which the volume of water present is less than about 1 percent.

2. A process according to claim 1 in which $R^2$ is hydrogen, halogen, lower alkoxy or lower haloalkoxy.

3. A process according to claim 1 in which $R^3$ and $R^4$ are halogen and $R^2$ is hydrogen.

4. A process according to claim 1 in which X is hydrogen or an alkali metal cation.

5. A process according to claim 1 in which $R^1$ is lower alkyl.

6. A process according to claim 1 in which the volume of water present is from about 0.01 to about 0.5%.

7. A process according to claim 1 in which the reaction is performed in the presence of a base.

8. A process according to claim 1 in which the reaction is performed in an ether solvent.

9. A process according to claim 9 in which the ether solvent is tetrahydrofuran, diisopropyl ether, tert-butyl methyl ether, diglyme or diethyl ether.

10. A process according to claim 7 in which the volume of water present is from about 0.01 to about 0.5%.

11. A process according to claim 7 in which the reaction is performed in an ether solvent.

12. A process according to claim 11 in which the ether solvent is tetrahydrofuran, diisopropyl ether, tert-butyl methyl ether, diglyme or diethyl ether.

13. A process according to claim 2 in which X is hydrogen or an alkali metal cation.

14. A process according to claim 2 in which $R^1$ is lower alkyl.

15. A process according to claim 2 in which X is hydrogen or an alkali metal cation.

16. A process according to claim 3 in which $R^1$ is lower alkyl.

17. A process according to claim 10 in which X is hydrogen or an alkali metal cation.

18. A process according to claim 10 in which $R^1$ is lower alkyl.

19. A process according to claim 1 in which the reaction is performed at a temperature from $-80°$ C. to the boiling point of the solvent.

20. A process according to claim 19 in which the reaction is performed at a temperature from $-20°$ C. to $60°$ C.

21. A process according to claim 1 in which the molar ratio of the 2,4-dihaloacetophenone:thiolating agent is from 1:1 to 1:2.

22. A process according to claim 21 in which the molar ratio of the 2,4-dihaloacetophenone:thiolating agent is from 1:1 to 1:1.5.

23. A process according to claim 19 in which the molar ratio of the 2,4-dihaloacetophenone:thiolating agent is from 1:1 to 1:2.

24. A process according to claim 23 in which the molar ratio of the 2,4-dihaloacetophenone:thiolating agent is from 1:1 to 1:1.5.

25. A process according to claim 20 in which the molar ratio of the 2,4-dihaloacetophenone:thiolating agent is from 1:1 to 1:2.

26. A process according to claim 25 in which the molar ratio of the 2,4-dihaloacetophenone:thiolating agent is from 1:1 to 1:1.5.

27. A process for preparing a 2-(thiosubstituted)-3,4-dichloroacetophenone of formula (Ia):

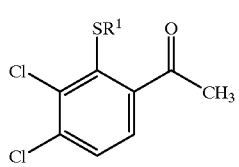

where $R^1$ is lower alkyl, or phenyl which is unsubstituted or is substituted by from one to five groups which are the same or different selected from the group consisting of halogen, lower alkyl, lower haloalkyl, lower alkoxy, lower haloalkoxy and —$S(O)_nR^5$;

n is zero, one or two; and $R^5$ is lower alkyl, or phenyl which is unsubstituted or substituted by from one to five groups which are the same or different selected from the group consisting of halogen, lower alkyl, lower haloalkyl, lower alkoxy, lower haloalkoxy and —$S(O)_n$-alkyl;

said process comprising reacting 2,3,4-trichloroacetophenone with a thiolating agent of formula (III):

$$R^1S-X \qquad (III)$$

wherein $R^1$ is as defined above and X is hydrogen or a metal cation, under substantially anhydrous conditions in which the volume of water present is less than about 1 percent.

* * * * *